United States Patent
Warad et al.

(10) Patent No.: US 11,718,607 B2
(45) Date of Patent: Aug. 8, 2023

(54) ATYPICAL COUPLING METHOD FOR THE PREPARATION OF 1,2-DI(THIOPHEN-2-YL)ETHENE-1,2-DIOL COMPOUNDS VIA A CU(II) CATALYST

(71) Applicant: QATAR UNIVERSITY, Doha (QA)

(72) Inventors: Ismail K. Warad, Doha (QA); Amjad M. Shraim, Doha (QA); Anas Al-Ali, Nablus (PS); Kifah S M Salih, Doha (QA); Abdelkader Zarrouk, Agdal-Rabat (MA); Yousef Hijji, Elkridge, MD (US)

(73) Assignee: QATAR UNIVERSITY, Doha (QA)

( * ) Notice: Subject to any disclaimer, the term of this patent is extended or adjusted under 35 U.S.C. 154(b) by 0 days.

(21) Appl. No.: 17/566,248

(22) Filed: Dec. 30, 2021

(65) Prior Publication Data

US 2022/0204487 A1  Jun. 30, 2022

Related U.S. Application Data

(60) Provisional application No. 63/133,113, filed on Dec. 31, 2020.

(51) Int. Cl.
*C07D 409/06* (2006.01)
*B01J 31/16* (2006.01)

(52) U.S. Cl.
CPC ........ *C07D 409/06* (2013.01); *B01J 31/1616* (2013.01)

(58) Field of Classification Search
CPC .................................................. C07D 409/06
See application file for complete search history.

(56) References Cited

U.S. PATENT DOCUMENTS

| 7,989,583 B2 | 8/2011 | Percino Zacarias et al. |
| 10,017,474 B1 * | 7/2018 | Al-Zeqri .............. C07D 213/30 |

OTHER PUBLICATIONS

Nabil Al-Zaqri et al., "Synthesis, physicochemical, thermal, and XRD/HSA interactions of mixed [Cu(Bipy)(Dipn)](X)2 complexes: DNA binding and molecular docking evaluatiion", Journal of Coordination Chemistry, ISSN: Journal homepage: https://www.tandfonline.com/loi/gcoo20, Published online: Nov. 5, 2020, https://doi.org/10.1080/00958972.2020.1841898, 14 pages.

Maddali L.N. Rao, et al., "Pd-catalyzed protecting-group-free crosscouplings of iodophenols with atom-economic triarylbismuth reagents", Tetrahedron Letters 61 (2020) 151512, journal homepage: www.elsevier.com/locate/tetlet, available online Dec. 12, 2019, https://doi.org/10.1016/j.tetlet.2019.151512, 6 pages.

Arpal Pal et al., "Copper-Catalyzed Chemoselective Cross-Coupling Reaction of Thioamides and α-Diazocarbonyl Compounds: Synthesis of Enaminones", University of Tulsa, Department of Chemistry and Biochemistry, http://www.elsevier.com/open-access/userlicense/1.0/, 5 pages, 2017.

Fu-She Han, "Transition-metal-catalyzed Suzuki-Miyaura cross-coupling reactions: a remarkable advance from passadium to mickel catalysts", Chem. soc. Rev., 2013, 42, 5270-5298, RSCPublishing, Received Dec. 20, 2012, The Royal Society of Chemistry, DOI:10.1039/c3cs35521g, www.rsc.org/csr, 29 pages.

Hojat Veisi et al., "Pd(II)/Pd(0) anchored to magnetic nanoparticles (Fe3O4) modified with biguanidine-chitosan polymer as a novel nanocatalyst for Suzuki-Miyaura coupling reactions", International Journal of Biological Macromolecules 113 (2018) 186-194, http://www.elsevier.com/locate/ijbiomac, https://doi.org/10.1016/j.ijbiomac.201 8.02.120, 9 pages.

Moises Perez-Lorenzo, "Palladium Nanoparticles as Efficient Catalysts for Suzuki Cross-Coupling Reactions", The Journal of Physical Chemistry Letters 2012, 3, 167-174, ACS Publications, 2011 American Chemical Society, Published Dec. 28, 2011, dx.doi.org/10.1021/jz2013984, 8 pages.

* cited by examiner

*Primary Examiner* — Matthew P Coughlin
(74) *Attorney, Agent, or Firm* — Squire Patton Boggs (US) LLP (57) ABSTRACT

Presented herein is a coupling method for the preparation of 1,2-di(thiophen-2-yl)ethane-1,2-diol compounds, including (E)-1,2-di(thiophen-2-yl)ethene-1,2-diol, via a Cu(II) catalyst.

22 Claims, 4 Drawing Sheets

ATYPICAL COUPLING METHOD FOR THE PREPARATION OF 1,2-DI(THIOPHEN-2-YL)ETHENE-1,2-DIOL COMPOUNDS VIA A CU(II) CATALYST

This application claims priority to, and the benefit of, U.S. Provisional Patent Application No. 63/133,113 filed Dec. 31, 2020. The entirety of this application is incorporated herein by reference for all purposes.

FIELD

Presented herein is a coupling method for the preparation of 1,2-di(thiophen-2-yl)ethane-1,2-diol compounds, including (E)-1,2-di(thiophen-2-yl)ethene-1,2-diol, via a Cu(II) catalyst.

BACKGROUND

In recent years, chemists have devoted tremendous efforts to developing and preparing novel cross-coupling catalysts (Rao, M. L. N., et al. *Tetrahedron Letters*, 2020; 61(8): 151512; Pal, A., et al., *Tetrahedron Letters*, 2017. 58(6): 586-589). For example, the Pd-catalyzed Suzuki coupling of $Ar^1X$ with $Ar^2B(OH)_2$ is one of the most famous coupling methods for the preparation of $Ar^1$—$Ar^2$ using transition metal complexes (Veisi, H., et al. *International Journal of Biological Macromolecules*, 2018, 113: 186-194; Perez-Lorenzo, et al. *Journal of Physical Chemistry Letters*, 2012. 3(2): 167-174).

Thiophenes, and in particular 1,2-di(thiophen-2-yl)ethane-1,2-diol compounds, represent an important class of heterocyclic molecules for organic synthesis, material synthesis, and pharmaceutical sciences. For example, (E)-1,2-di(thiophen-2-yl)ethene-1,2-diol is an important building block for the preparation of chemotherapeutic agents, and the presence of two hydroxyl groups provides for potent antibacterial, antifungal, and antiviral activity. Due to its solubility in water, (E)-1,2-di(thiophen-2-yl)ethene-1,2-diol can be employed in cream formulations (e.g., glycerin derivatives) intended for skin protection from the hazards of UV-sunlight radiation. Further, the presence of two hydroxyl groups allows (E)-1,2-di(thiophen-2-yl)ethene-1,2-diol to form epoxides.

(E)-1,2-Di(thiophen-2-yl)ethene-1,2-diol is a florescent water-soluble compound that can be used as optical active material. This is especially beneficial because most optically active agents are not soluble in water. Additionally, due to the chelating properties of the O,S-containing ligand, the compound can act as an ionic heavy metal chelator to be used, for example, in sensing heavy metals in groundwater. Lastly, (E)-1,2-di(thiophen-2-yl)ethene-1,2-diol, functionalized with several unsaturated carbon-carbon bonds and trans hydroxyl groups, can be utilized in the synthesis of new chemical compounds.

Given the importance of (E)-1,2-di(thiophen-2-yl)ethene-1,2-diol compounds as building blocks for organic synthesis, material sciences, and pharmaceutical compositions, it would be useful to provide advantageous processes for their production.

SUMMARY OF THE INVENTION

Described herein is an unconventional, safe, mild, and rapid coupling method for the synthesis of (E)-1,2-di(thiophen-2-yl)ethene-1,2-diol with high yield and purity from thiophene-2-carbaldehyde. This coupling method utilizes a Cu(II) catalyst, which is advantageous because it is abundant, cheap, and environmentally-friendly compared to typical palladium or platinum catalysts.

In one aspect, the method is the synthesis of (E)-1,2-di(thiophen-2-yl)ethene-1,2-diol from the dimerization of thiophene-2-carbaldehyde in the presence of a Cu(II) catalyst:

In one embodiment, the Cu(II) catalyst is a homogenous Cu(II) complex of 1,10-phenanthroline (phen) and diamine (a copper(II)/phen/diamine catalyst) of Formula A:

wherein:
n is an integer selected from 1 and 2;
R is independently selected from —H, —CH₃, and —CH₂CH₂OH; and
X⁻ is Cl⁻, Br⁻, or NO₃⁻.

In one embodiment, the Cu(II) catalyst is a catalyst of Formula A and the amount of the catalyst of Formula A is between about 0.05% and 10.0% by weight of thiophene-2-carbaldehyde. In one embodiment, the Cu(II) catalyst is a catalyst of Formula A and the amount of the catalyst of Formula A is between about 0.1% and 5.0% by weight of thiophene-2-carbaldehyde. In one embodiment, the Cu(II) catalyst is a catalyst of Formula A and the amount of the catalyst of Formula A is between about 0.1% and 2.5% by weight of thiophene-2-carbaldehyde. In one embodiment, the Cu(II) catalyst is a catalyst of Formula A and the amount of the catalyst of Formula A is between about 0.5% and 2.0% by weight of thiophene-2-carbaldehyde. In one embodiment, the Cu(II) catalyst is a catalyst of Formula A and the amount of the catalyst of Formula A is at least about 0.1%, at least about 0.2% at least about 0.5%, at least about 1.0%, at least about 1.5%, or at least about 2.0% by weight of thiophene-2-carbaldehyde. In one embodiment, the Cu(II) catalyst is a catalyst of Formula A and the amount of the catalyst of Formula A is less than about 10.0%, less than about 8.0%, less than about 5.0%, less than about 2.5%, less than about 1.0%, less than 0.5%, or less than 0.1% by weight of thiophene-2-carbaldehyde. In one embodiment, the Cu(II) catalyst is a catalyst of Formula A and the amount of the catalyst of Formula A is about 1.0% by weight of thiophene-2-carbaldehyde.

In certain embodiments, the turnover number (TON) of the Cu(II) catalyst of Formula A is between about 800 and 1500, between about 1000 and 1400, or between about 1100 and 1300. In one embodiment, the TON is at least about 1000. In one embodiment, the TON is about 1000.

In one embodiment, the synthesis is conducted in an aqueous medium. In certain embodiments, the synthesis is conducted in a polar aprotic solvent/water system, including, but not limited to THF/water, acetone/water, DMF/water, ACN/water, and DMSO/water. In one embodiment, the synthesis is conducted in THF/water.

In one embodiment, the synthesis is conducted at room temperature.

In one embodiment, the synthesis is conducted in TFH/water and the amount of the Cu(II) catalyst of Formula A is about 1.0% by weight of thiophene-2-carbaldehyde.

DETAILED DESCRIPTION

Described herein is novel and advantageous coupling method for the synthesis of (E)-1,2-di(thiophen-2-yl)ethene-1,2-diol in the presence of a Cu(II) catalyst that results in high yield and purity. This preparation method also helps to provide a better understanding of coupling reactions using Cu(II) catalysts.

In one aspect, the method is the synthesis of (E)-1,2-di(thiophen-2-yl)ethene-1,2-diol from the dimerization of thiophene-2-carbaldehyde in the presence of a Cu(II) catalyst:

In one embodiment, the Cu(II) catalyst is a homogenous Cu(II) complex of 1,10-phenanthroline (phen) and diamine (a copper(II)/phen/diamine catalyst) of Formula A:

wherein:

n is an integer selected from 1 and 2;

R is independently selected from —H, —CH$_3$, and —CH$_2$CH$_2$OH; and

X$^-$ is Cl$^-$, Br$^-$, or NO$_3^-$.

In one embodiment, n is 1. In one embodiment, n is 2.

In one embodiment, including any of the foregoing, R is —H. In one embodiment, including any of the foregoing, R is —CH$_3$. In one embodiment, including any of the foregoing, R is —CH$_2$CH$_2$OH.

In one embodiment, including any of the foregoing, X$^-$ is Cl$^-$. In one embodiment, including any of the foregoing, X$^-$ is Br$^-$. In one embodiment, including any of the foregoing, X$^-$ is NO$_3^-$.

In one embodiment, R is —H, X$^-$ is Cl$^-$, and n is 1. In one embodiment, R is —H, X$^-$ is Cl$^-$, and n is 2. In one embodiment, R is —H, X$^-$ is Br$^-$, and n is 1. In one embodiment, R is —H, X$^-$ is Br$^-$, and n is 2. In one embodiment, R is —H, X$^-$ is NO$_3^-$, and n is 1. In one embodiment, R is —H, X$^-$ is NO$_3^-$, and n is 2.

In one embodiment, R is —CH$_3$, X$^-$ is Cl$^-$, and n is 1. In one embodiment, R is —CH$_3$, X$^-$ is Cl$^-$, and n is 2. In one embodiment, R is —CH₃, X⁻ is Br⁻, and n is 1. In one embodiment, R is —CH₃, X⁻ is Br⁻, and n is 2. In one embodiment, R is —CH₃, X⁻ is NO₃⁻, and n is 1. In one embodiment, R is —CH₃, X⁻ is NO₃⁻, and n is 2.

In one embodiment, R is —CH₂CH₂OH, X⁻ is Cl⁻, and n is 1. In one embodiment, R is —CH₂CH₂OH, X⁻ is Cl⁻, and n is 2. In one embodiment, R is —CH₂CH₂OH, X⁻ is Br⁻, and n is 1. In one embodiment, R is —CH₂CH₂OH, X⁻ is Br⁻, and n is 2. In one embodiment, R is —CH₂CH₂OH, X⁻ is NO₃⁻, and n is 1. In one embodiment, R is —CH₂CH₂OH, X⁻ is NO₃⁻, and n is 2.

In one embodiment, the Cu(II) complex of Formula A is selected from:

and

In one embodiment, the Cu(II) complex of Formula A is selected from:

and

In one embodiment, the Cu(II) complex of Formula A is selected from:

and

In one embodiment, the Cu(II) complex of Formula A is selected from:

and

In one embodiment, the Cu(II) complex of Formula A is selected from:

and

In one embodiment, the Cu(II) complex of Formula A is selected from:

and

In one embodiment, the Cu(II) complex of Formula A is selected from:

and

In one embodiment, the amount of the Cu(II) catalyst is between about 0.05% and 10.0%, between about 0.1% and 5.0%, between about 0.5% and 3.0%, between about 1.0% and 5.0%, or between 3.0% and 5.0% by weight of thiophene-2-carbaldehyde. In one embodiment, the amount of the Cu(II) catalyst is between about 0.25% and 3.0%, between about 0.25% and 2.0%, or between about 0.25% and 1.5% by weight of thiophene-2-carbaldehyde. In one embodiment, the amount of the Cu(II) catalyst is between about 3.0% and 10.0%, between about 4.0% and 0.09%, or between about 5.0% and 8.0% by weight of thiophene-2-carbaldehyde. In one embodiment, the amount of the Cu(II) catalyst is between about 3.0% and 5.0% by weight of thiophene-2-carbaldehyde.

In one embodiment, the amount of the Cu(II) catalyst is between about 0.05 mol % and 5.0 mol %, between about 0.05 mol % and 3.0 mol %, between about 0.1 mol % and 5.0 mol %, or between 0.1 mol % and 3.0 mol %. In one embodiment, the amount of the Cu(II) catalyst is between about 0.25 mol % and 3.0 mol %, between about 0.25 mol % and 2.0 mol %, or between about 0.25 mol % and 1.5 mol %. In one embodiment, the amount of the Cu(II) catalyst is between about 0.5 mol % and 1.0 mol %. In one embodiment, the amount of the Cu(II) catalyst is about 0.1 mol %.

In one embodiment, the Cu(II) catalyst is of a catalyst of Formula A and the amount of the Cu(II) catalyst of Formula A is between about 0.05% and 10.0%, between about 0.1% and 5.0%, between about 0.5% and 3.0%, between about 1.0% and 5.0%, or between 3.0% and 5.0% by weight of thiophene-2-carbaldehyde. In one embodiment, the Cu(II) catalyst is of a catalyst of Formula A and the amount of the Cu(II) catalyst of Formula A is between about 0.25% and 3.0%, between about 0.25% and 2.0%, or between about 0.25% and 1.5% by weight of thiophene-2-carbaldehyde. In one embodiment, the Cu(II) catalyst is of a catalyst of Formula A and the amount of the Cu(II) catalyst of Formula A is between about 3.0% and 10.0%, between about 4.0% and 9.0%, or between about 5.0% and 8.0% by weight of thiophene-2-carbaldehyde. In one embodiment, the Cu(II) catalyst is of a catalyst of Formula A and the amount of the Cu(II) catalyst of Formula A is between about 3.0% and 5.0% by weight of thiophene-2-carbaldehyde. In one embodiment, the Cu(II) catalyst is of a catalyst of Formula A and the amount of the Cu(II) catalyst of Formula A is about 1.0% by weight of thiophene-2-carbaldehyde.

In one embodiment, the Cu(II) catalyst is a catalyst of Formula A wherein R is —H, X⁻ is Cl⁻, and n is 1 and the amount of the catalyst of Formula A is about 1.0% by weight of thiophene-2-carbaldehyde. In one embodiment, the Cu(II) catalyst is a catalyst of Formula A wherein R is —H, X⁻ is Cl⁻, and n is 2 and the amount of the catalyst of Formula A is about 1.0% by weight of thiophene-2-carbaldehyde. In one embodiment, the Cu(II) catalyst is a catalyst of Formula A wherein R is —H, X⁻ is Br⁻, and n is 1 and the amount of the catalyst of Formula A is about 1.0% by weight of thiophene-2-carbaldehyde. In one embodiment, the Cu(II) catalyst is a catalyst of Formula A wherein R is —H, X⁻ is Br⁻, and n is 2 and the amount of the catalyst of Formula A is about 1.0% by weight of thiophene-2-carbaldehyde. In one embodiment, the Cu(II) catalyst is a catalyst of Formula A wherein R is —H, X⁻ is NO₃⁻, and n is 1 and the amount of the catalyst of Formula A is about 1.0% by weight of thiophene-2-carbaldehyde. In one embodiment, the Cu(II) catalyst is a catalyst of Formula A wherein R is —H, X⁻ is NO₃⁻, and n is 2 and the amount of the catalyst of Formula A is about 1.0% by weight of thiophene-2-carbaldehyde.

In one embodiment, the Cu(II) catalyst is a catalyst of Formula A wherein R is —CH₃, X⁻ is Cl⁻ and n is 1 and the amount of the catalyst of Formula A is about 1.0% by weight of thiophene-2-carbaldehyde. In one embodiment, the Cu(II) catalyst is a catalyst of Formula A wherein R is —CH₃, X⁻ is Cl⁻ and n is 2 and the amount of the catalyst of Formula A is about 1.0% by weight of thiophene-2-carbaldehyde. In one embodiment, the Cu(II) catalyst is a catalyst of Formula A wherein R is —CH₃, X⁻ is Br⁻, and n is 1 and the amount of the catalyst of Formula A is about 1.0% by weight of thiophene-2-carbaldehyde. In one embodiment, the Cu(II) catalyst is a catalyst of Formula A wherein R is —CH₃, X⁻ is Br⁻, and n is 2 and the amount of the catalyst of Formula A is about 1.0% by weight of thiophene-2-carbaldehyde. In one embodiment, the Cu(II) catalyst is a catalyst of Formula A wherein R is —CH₃, X⁻ is NO₃⁻, and n is 1 and the amount of the catalyst of Formula A is about 1.0% by weight of thiophene-2-carbaldehyde. In one embodiment, the Cu(II) catalyst is a catalyst of Formula A wherein R is —CH₃, X⁻ is NO₃⁻, and n is 2 and the amount of the catalyst of Formula A is about 1.0% by weight of thiophene-2-carbaldehyde.

In one embodiment, the Cu(II) catalyst is a catalyst of Formula A wherein R is —CH₂CH₂OH, X⁻ is Cl⁻, and n is 1 and the amount of the catalyst of Formula A is about 1.0% by weight of thiophene-2-carbaldehyde. In one embodiment, the Cu(II) catalyst is a catalyst of Formula A wherein R is —CH₂CH₂OH, X⁻ is Cl⁻, and n is 2 and the amount of the catalyst of Formula A is about 1.0% by weight of thiophene-2-carbaldehyde. In one embodiment, the Cu(II) catalyst is a catalyst of Formula A wherein R is —CH₂CH₂OH, X⁻ is Br⁻, and n is 1 and the amount of the catalyst of Formula A is about 1.0% by weight of thiophene-2-carbaldehyde. In one embodiment, the Cu(II) catalyst is a catalyst of Formula A wherein R is —CH₂CH₂OH, X⁻ is Br⁻, and n is 2 and the amount of the catalyst of Formula A is about 1.0% by weight of thiophene-2-carbaldehyde. In one embodiment, the Cu(II) catalyst is a catalyst of Formula A wherein R is —CH₂CH₂OH, X⁻ is NO₃⁻, and n is 1 and the amount of the catalyst of Formula A is about 1.0% by weight of thiophene-2-carbaldehyde. In one embodiment, the Cu(II) catalyst is a catalyst of Formula A wherein R is —CH₂CH₂OH, X⁻ is NO₃⁻, and n is 2 and the amount of the catalyst of Formula A is about 1.0% by weight of thiophene-2-carbaldehyde.

In one embodiment, the synthesis is conducted in an aqueous medium. In certain embodiments, the synthesis is conducted in a polar aprotic solvent/water system, including, but not limited to tetrahydrofuran (THF)/water, acetone/water, DMF/water, ACN/water, and DMSO/water. In one embodiment, the synthesis is conducted in THF/water. In certain embodiments, the ratio of polar aprotic solvent:water is about 4:1, about 3:1, about 2:1, about 1:1, about 1:2, about 1:3, or about 1:4. In one embodiment, the ratio of polar aprotic solvent:water is about 1:1.

In one embodiment, the synthesis is conducted in one or more organic solvent(s), for example a polar aprotic solvent, including, but not limited to THF, acetone, DMF, ACN, and DMSO.

In one embodiment, the synthesis is conducted in the aqueous medium or an organic solvent at a concentration of the thiophene-2-carbaldehyde of at least about 0.1 molar. In certain embodiments, the concentration of the thiophene-2-carbaldehyde is at least about 0.15 molar, at least about 0.2 molar, at least about 0.25 molar, at least about 0.3 molar, at least about 0.5 molar, at least about 0.7 molar, at least about 1.0 molar, at least about 1.2 molar, at least about 1.5 molar, at least about 2.0 molar, or more.

In certain embodiments, the polar aprotic solvent is a C₂-C₈ ether, including, but not limited to THF, methyl-t-butyl ether (MTBE), and dioxane.

In certain embodiments, the polar aprotic solvent is a C₃-C₇ ketone, including, but not limited to acetone, propanone, and methyl isobutyl ketone.

In certain embodiments, the polar aprotic solvent is a C₃-C₇ nitrile, including, but not limited to acetonitrile (ACN) or propionitrile.

In certain embodiments, the polar aprotic solvent is DMF.

In certain embodiments, the polar aprotic solvent is DMSO.

In certain embodiments, the synthesis is conducted in an alcohol or an alcohol/water system. In one embodiment, the alcohol is a C₁-C₈ alcohol, including, but not limited to methanol, ethanol, or n-propanol. In certain embodiments, the ratio of alcohol:water is about 4:1, about 3:1, about 2:1, about 1:1, about 1:2, about 1:3, or about 1:4.

Reaction times and reaction conditions (e.g., temperature, atmosphere, etc.) will vary and may be determined by reference to the examples and disclosure provided herein, as well as routine experimentation and consultation of the relevant literature when necessary. In some embodiments, the processes described herein are run under such conditions so as to achieve the desired result.

In one embodiment, the synthesis is conducted at room temperature, i.e. a temperature between about 20° C. and 25° C., but may be performed at a higher temperature if deemed necessary, i.e., at a temperature of greater than about 20° C., greater than about 25° C., greater than about 30° C., greater than about 35° C., or about 40° C.

In one embodiment, the reaction is stirred for at least about 20 hours, at least about 15 hours, at least about 12 hours, at least about 10 hours, at least about 8 hours, at least about 4 hours, or at least about 2 hours.

In one embodiment, the reaction is stirred for no more than 30 minutes, no more than 1 hour, no more than 2 hours, no more than 4 hours, no more than 6 hours, no more than 8 hours, no more than 10 hours, no more than 12 hours, no more than 15 hours, or no more than 20 hours.

In one embodiment, the reaction is conducted in open atmosphere and at ambient-light conditions.

In some embodiments, including any of the foregoing, the synthesis of (E)-1,2-di(thiophen-2-yl)ethene-1,2-diol from the dimerization of thiophene-2-carbaldehyde in the presence of a Cu(II) catalyst affords pure (E)-1,2-di(thiophen-2-yl)ethene-1,2-diol product that is substantially or exclusively the E-isomer. In some embodiments, including any of the foregoing, the synthesis of (E)-1,2-di(thiophen-2-yl) ethene-1,2-diol from the dimerization of thiophene-2-carbaldehyde in the presence of a Cu(II) catalyst affords pure (E)-1,2-di(thiophen-2-yl)ethene-1,2-diol product that is about 90% or greater of the E-isomer over the Z-isomer. In certain embodiments, including any of the foregoing, the (E)-1,2-di(thiophen-2-yl)ethene-1,2-diol product is about 93% pure or greater, about 95% pure or greater, about 97% pure or greater, about 98% pure or greater, about 99% pure or greater, or even about 100% pure. In one embodiment, including any of the foregoing, the synthesis of (E)-1,2-di(thiophen-2-yl)ethene-1,2-diol from the dimerization of thiophene-2-carbaldehyde in the presence of a Cu(II) catalyst affords (E)-1,2-di(thiophen-2-yl)ethene-1,2-diol product that is about 100% the E-isomer.

In some embodiments, the method may further include purification and isolation steps to remove impurities and/or reactants from the product. Furthermore, if the product contains a mixture of E-isomer and Z-isomer products, the product may be purified to remove the undesired Z-isomer. In one embodiment, the product is about 100% the E-isomer and purification is to remove reactants and/or impurities other than the Z-isomer from the product.

In one aspect, the method is the synthesis of (E)-1,2-di(thiophen-2-yl)ethene-1,2-diol comprising the steps of (1) the coupling of two molecules of thiophene-2-carbaldehyde in the presence of a Cu(II) catalyst to afford crude (E)-1,2-di(thiophen-2-yl)ethene-1,2-diol:

and
(2) further optionally purifying the crude (E)-1,2-di(thiophen-2-yl)ethene-1,2-diol from step (1) to afford pure (E)-1,2-di(thiophen-2-yl)ethene-1,2-diol.

Purification of E-isomer-enriched (E)-1,2-di(thiophen-2-yl)ethene-1,2-diol can be obtained by selective crystallization in a solvent or solvent/anti-solvent system, column chromatography, or any method known to skilled chemists that results in such purification.

Non-limiting examples of the crystallization solvents are polar organic solvents such as alkyl esters, for example ethyl acetate, acetonitrile, DMSO, methylene chloride, acetone, or the like. Non-limiting examples of suitable anti-solvents are non-polar organic liquids such as hydrocarbons that can be removed from the final product, including but not limited to pentane, hexane, heptane, or the like.

In certain embodiments, the purification in step (2) is the selective crystallization of the crude (E)-1,2-di(thiophen-2-yl)ethene-1,2-diol, for example, in an alkyl acetate solvent such as ethyl acetate, a chlorinated solvent, such a dichloromethane, a ketone solvent, such as acetone, or a mixture thereof to afford pure (E)-1,2-di(thiophen-2-yl)ethene-1,2-diol. In one embodiment, the crystallization is conducted in a chlorinated solvent, such as dichloromethane. In certain embodiments, the purification is conducted via selective crystallization from a chlorinated solvent with acetonitrile or an aliphatic hydrocarbon. In one embodiment, the purification in step (2) is the selective crystallization of crude (E)-1,2-di(thiophen-2-yl)ethene-1,2-diol wherein crude (E)-1,2-di(thiophen-2-yl)ethene-1,2-diol is dissolved in an organic solvent and then an anti-solvent is added dropwise to the above solution system wherein the organic solvent comprises, for example, a solvent selected from $C_{1-8}$ alcohol(s), $C_{2-8}$ ether(s), $C_{3-7}$ ketone(s), $C_{3-7}$ ester(s), $C_{1-2}$ chlorocarbon(s), and $C_{2-7}$ nitrile(s) or a mixture thereof and wherein the anti-solvent comprises a solvent that is not substantially miscible with the solvent, such as a $C_{5-12}$ saturated hydrocarbon(s), $C_{6-12}$ aromatic hydrocarbon(s), or petroleum ether.

In one embodiment, including any of the foregoing, the method of synthesizing (E)-1,2-di(thiophen-2-yl)ethene-1,2-diol comprises the steps of (a) dissolving thiophene-2-carbaldehyde in a polar aprotic solvent/water system; (b) adding a Cu(II) catalyst of Formula A in an amount that is between about 0.05% and 10.0% by weight of the thiophene-2-carbaldehyde; and (c) stirring at room temperature until the reaction is complete to afford pure (E)-1,2-di(thiophen-2-yl)ethene-1,2-diol.

In one embodiment, including any of the foregoing, the method of synthesizing (E)-1,2-di(thiophen-2-yl)ethene-1,2-diol comprises the steps of (a) dissolving thiophene-2-carbaldehyde in a polar aprotic solvent/water system; (b) adding a Cu(II) catalyst of Formula A in an amount that is between about 0.05% and 10.0% by weight of the thiophene-2-carbaldehyde; (c) stirring at room temperature until the reaction is complete to afford crude (E)-1,2-di(thiophen-2-yl)ethene-1,2-diol; and, (d) further purifying the crude (E)-1,2-di(thiophen-2-yl)ethene-1,2-diol to afford pure (E)-1,2-di(thiophen-2-yl)ethene-1,2-diol.

In one embodiment, including any of the foregoing, the polar aprotic solvent/water system is THF/water and the Cu(II) catalyst of Formula A is added in an amount that is between about 0.05% and 5.0% by weight of the thiophene-2-carbaldehyde. In one embodiment, including any of the foregoing, the polar aprotic solvent/water system is THF/water and the Cu(II) catalyst of Formula A is added in an amount that is between about 0.05% and 3.0% by weight of the thiophene-2-carbaldehyde. In one embodiment, including any of the foregoing, the polar aprotic solvent/water system is THF/water and the Cu(II) catalyst of Formula A is added in an amount that is between about 0.5% and 2.0% by weight of the thiophene-2-carbaldehyde.

In one embodiment, including any of the foregoing, the polar aprotic solvent/water system is acetone/water and the Cu(II) catalyst of Formula A is added in an amount that is between about 0.05% and 5.0% by weight of the thiophene-2-carbaldehyde. In one embodiment, including any of the foregoing, the polar aprotic solvent/water system is acetone/water and the Cu(II) catalyst of Formula A is added in an amount that is between about 0.05% and 3.0% by weight of the thiophene-2-carbaldehyde. In one embodiment, including any of the foregoing, the polar aprotic solvent/water system is acetone/water and the Cu(II) catalyst of Formula A is added in an amount that is between about 0.5% and 2.0% by weight of the thiophene-2-carbaldehyde.

In one embodiment, including any of the foregoing, the polar aprotic solvent/water system is ACN/water and the Cu(II) catalyst of Formula A is added in an amount that is between about 0.05% and 5.0% by weight of the thiophene-2-carbaldehyde. In one embodiment, including any of the foregoing, the polar aprotic solvent/water system is ACN/water and the Cu(II) catalyst of Formula A is added in an amount that is between about 0.05% and 3.0% by weight of the thiophene-2-carbaldehyde. In one embodiment, including any of the foregoing, the polar aprotic solvent/water system is ACN/water and the Cu(II) catalyst of Formula A is added in an amount that is between about 0.5% and 2.0% by weight of the thiophene-2-carbaldehyde.

In one embodiment, including any of the foregoing, the method of synthesizing (E)-1,2-di(thiophen-2-yl)ethene-1,2-diol comprises the steps of (a) dissolving thiophene-2-carbaldehyde in a polar aprotic solvent; (b) adding a Cu(II) catalyst of Formula A in an amount that is between about 0.05% and 10.0% by weight of the thiophene-2-carbaldehyde; and, (c) stirring at room temperature until the reaction is complete to afford pure (E)-1,2-di(thiophen-2-yl)ethene-1,2-diol.

In one embodiment, including any of the foregoing, the method of synthesizing (E)-1,2-di(thiophen-2-yl)ethene-1,2-diol comprises the steps of (a) dissolving thiophene-2-carbaldehyde in a polar aprotic solvent system; (b) adding a Cu(II) catalyst of Formula A in an amount that is between about 0.05% and 10.0% by weight of the thiophene-2-carbaldehyde; (c) stirring at room temperature until the reaction is complete to afford crude (E)-1,2-di(thiophen-2-yl)ethene-1,2-diol; and (d) further purifying the crude (E)-1,2-di(thiophen-2-yl)ethene-1,2-diol to afford pure (E)-1,2-di(thiophen-2-yl)ethene-1,2-diol.

In one embodiment, including any of the foregoing, the polar aprotic solvent is THF and the Cu(II) catalyst of Formula A is added in an amount that is between about 0.05% and 5.0% by weight of the thiophene-2-carbaldehyde. In one embodiment, including any of the foregoing, the polar aprotic solvent is THF and the Cu(II) catalyst of Formula A is added in an amount that is between about 0.05% and 3.0% by weight of the thiophene-2-carbaldehyde. In one embodiment, including any of the foregoing, the polar aprotic solvent is THF and the Cu(II) catalyst of Formula A is added in an amount that is between about 0.5% and 2.0% by weight of the thiophene-2-carbaldehyde.

In one embodiment, including any of the foregoing, the polar aprotic solvent is acetone and the Cu(II) catalyst of Formula A is added in an amount that is between about 0.05% and 5.0% by weight of the thiophene-2-carbaldehyde. In one embodiment, including any of the foregoing, the polar aprotic solvent is acetone and the Cu(II) catalyst of Formula A is added in an amount that is between about 0.25% and 3.0% by weight of the thiophene-2-carbaldehyde. In one embodiment, including any of the foregoing, the polar aprotic solvent is acetone and the Cu(II) catalyst of Formula A is added in an amount that is between about 0.5% and 2.0% by weight of the thiophene-2-carbaldehyde.

In one embodiment, including any of the foregoing, the polar aprotic solvent is ACN and the Cu(II) catalyst of Formula A is added in an amount that is between about 0.25% and 5.0% by weight of the thiophene-2-carbaldehyde. In one embodiment, including any of the foregoing, the polar aprotic solvent is ACN and the Cu(II) catalyst of Formula A is added in an amount that is between about 0.25% and 3.0% by weight of the thiophene-2-carbaldehyde. In one embodiment, including any of the foregoing, the polar aprotic solvent is ACN and the Cu(II) catalyst of Formula A is added in an amount that is between about 0.5% and 2.0% by weight of the thiophene-2-carbaldehyde.

In one embodiment, including any of the foregoing, the method of synthesizing (E)-1,2-di(thiophen-2-yl)ethene-1,2-diol comprises the steps of (a) dissolving thiophene-2-carbaldehyde in an alcohol/water system; (b) adding a Cu(II) catalyst of Formula A in an amount that is between about 0.05% and 10.0% by weight of the thiophene-2-carbaldehyde; and, (c) stirring at room temperature until the reaction is complete to afford pure (E)-1,2-di(thiophen-2-yl)ethene-1,2-diol.

In one embodiment, including any of the foregoing, the method of synthesizing (E)-1,2-di(thiophen-2-yl)ethene-1,2-diol comprises the steps of (a) dissolving thiophene-2-carbaldehyde in an alcohol/water system; (b) adding a Cu(II) catalyst of Formula A in an amount that is between about 0.05% and 10.0% by weight of the thiophene-2-carbaldehyde; (c) stirring at room temperature until the reaction is complete to afford crude (E)-1,2-di(thiophen-2-yl)ethene-1,2-diol; and, (d) further purifying the crude (E)-1,2-di(thiophen-2-yl)ethene-1,2-diol to afford pure (E)-1,2-di(thiophen-2-yl)ethene-1,2-diol.

In one embodiment, including any of the foregoing, the alcohol/water system is MeOH/water and the Cu(II) catalyst of Formula A is added in an amount that is between about 0.25% and 5.0% by weight of the thiophene-2-carbaldehyde. In one embodiment, the alcohol/water system is MeOH/water and the Cu(II) catalyst of Formula A is added in an amount that is between about 0.25% and 3.0% by weight of the thiophene-2-carbaldehyde.

In one embodiment, including any of the foregoing, the alcohol/water system is EtOH/water and the Cu(II) catalyst of Formula A is added in an amount that is between about 0.25% and 5.0% by weight of the thiophene-2-carbaldehyde. In one embodiment, the alcohol/water system is EtOH/water and the Cu(II) catalyst of Formula A is added in an amount that is between about 0.25% and 3.0% by weight of the thiophene-2-carbaldehyde.

In some embodiments, including any of the foregoing, the (E)-1,2-di(thiophen-2-yl)ethene-1,2-diol product is substantially or exclusively the E-isomer. In some embodiments, including any of the foregoing, the (E)-1,2-di(thiophen-2-yl)ethene-1,2-diol product is about 90% or greater the E-isomer over the Z-isomer. In certain embodiments, including any of the foregoing, the (E)-1,2-di(thiophen-2-yl)ethene-1,2-diol product is about 93% or greater the E-isomer over the Z-isomer, about 95% or greater the E-isomer over the Z-isomer, about 97% or greater the E-isomer over the Z-isomer, about 98% or greater the E-isomer over the Z-isomer, about 99% or greater the E-isomer over the Z-isomer, or even about 100% the E-isomer. In one embodiment, including any of the foregoing, the (E)-1,2-di(thiophen-2-yl)ethene-1,2-diol product is about 100% the E-isomer.

In some embodiments, including any of the foregoing, the crude (E)-1,2-di(thiophen-2-yl)ethene-1,2-diol product is a mixture wherein the E-isomer is in excess of the R-isomer. In certain embodiments, including any of the foregoing, the ratio of E-isomer to R-isomer in crude (E)-1,2-di(thiophen-2-yl)ethene-1,2-diol product is greater than about 51:49, greater than about 55:45, greater than about 60:40, greater than about 65:35, greater than about 70:30, greater than about 85:15, greater than about 90:10, greater than about 95:5, greater than 98:2, or greater than 99:1.

In some embodiments, including any of the foregoing, the crude (E)-1,2-di(thiophen-2-yl)ethene-1,2-diol product is about 90% or greater the E-isomer over the Z-isomer. In certain embodiments, including any of the foregoing, the crude (E)-1,2-di(thiophen-2-yl)ethene-1,2-diol product is about 93% or greater the E-isomer over the Z-isomer, about 95% or greater the E-isomer over the Z-isomer, about 97% or greater the E-isomer over the Z-isomer, about 98% or greater the E-isomer over the Z-isomer, about 99% or greater the E-isomer over the Z-isomer, or even about 100% the E-isomer. In one embodiment, including any of the foregoing, the crude (E)-1,2-di(thiophen-2-yl)ethene-1,2-diol product is about 100% the E-isomer, and the purification removes reactants and/or impurities other than the E-isomer from the product.

Definitions

The terms "a" and "an" do not denote a limitation of quantity, but rather denote the presence of at least one of the referenced item. The term "or" means "and/or". Recitation of ranges of values merely intend to serve as a shorthand method of referring individually to each separate value falling within the range, unless otherwise indicated herein, and each separate value is incorporated into the specification as if it were individually recited herein. The endpoints of all ranges are included within the range and independently combinable. All processes described herein can be performed in a suitable order unless otherwise indicated herein or otherwise clearly contradicted by context. The use of example, or exemplary language (e.g., "such as"), is intended merely to better illustrate the invention and does not pose a limitation on the scope of the invention on unless otherwise claimed.

The compounds prepared by the processes of the present invention can exist as the E-isomer or the Z-isomer, and may exist, be used, or isolated in forms that are about 90% or greater the E-isomer. In alternative embodiments, the compounds are about 80% or greater the E-isomer or about 85% or greater the E-isomer.

"Pure" or "purified" as described herein, refers to the purity of a given E-isomer compound. For example, a compound is "purified" when the given E-isomer compound is a major component of the composition, i.e., at least 50% w/w pure. Thus, "purified" embraces at least 50% w/w purity, at least 60% w/w purity, at least 70% purity, at least 80% purity, at least 85% purity, at least 90% purity, at least 92% purity, at least 94% purity, at least 96% purity, at least 97% purity, at least 98% purity, at least 99% purity, at least 99.5% purity, and at least 99.9% purity, wherein "substantially pure" embraces at least 95% purity, at least 96% purity, at least 97% purity, at least 98% purity, at least 99% purity, at least 99.5% purity, and at least 99.9% purity. In some embodiments, the substantially pure compound is about 100% the E-isomer.

"Turnover number" or (TON) specifies the number of catalytic cycles that the catalyst can perform until it is deactivated under the reaction conditions described herein.

"Alkyl" is a branched or straight chain saturated aliphatic hydrocarbon group. In one non-limiting embodiment, the alkyl group contains from about 1 to about 6 carbon atoms, from about 1 to about 4 carbons, or from about 1 to about 3 carbons. Examples of alkyl include, but are not limited to, methyl, ethyl, n-propryl, isopropyl, n-butyl, sec-butyl, t-butyl, n-pentyl, tert-pentyl, neopentyl, and n-hexyl. Alkyl can also include cycloalkyl.

"Alkoxy" refers to the group —O—R', wherein R' is alkyl. Examples of alkoxy include, but are not limited to, methoxy, ethoxy, n-propoxy, isopropoxy, n-butoxy, tert-butoxy, sec-butoxy, n-pentoxy, and n-hexyloxy.

The term "cyano" refers to —CN.

The term "halo" refers to independently to bromo, chloro, fluoro, or iodo.

The term "nitro" refers to —$NO_2$.

Any compound used in or formed by the processes described herein may form a solvate with solvents (including water). Therefore, in one non-limiting embodiment, the invention includes a solvated form of the compound. The term "solvate" refers to a molecular complex of a compound of the present invention (including a salt thereof) with one or more solvent molecules. Non-limiting examples of solvent are water, ethanol, dimethyl sulfoxide, acetone, and other common organic solvents. The term "hydrate" refers to a molecular complex comprising a compound as described herein and water. Solvates in accordance with this disclosure include those wherein the solvent may be isotopically substituted, e.g. $D_2O$, de-acetone, and de-DMSO. A solvate can be in a liquid or solid form.

Any compound used in or formed by the processes described herein may be modified to make an inorganic or organic acid or base addition salt thereof to form a salt, if appropriate and desired. The salts of the present compounds can be prepared from a parent compound that contains a basic or acidic moiety by chemical processes. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are typical, where practicable. Salts of the present compounds may optionally be provided in the form of a solvate. Examples of salts include, but are not limited to, mineral or organic acid salts of basic residues such as amines; alkali or organic salts of acidic residues such as carboxylic acids; and the like. The salts include the salts and the quaternary ammonium salts of the parent compound formed, for example, from inorganic or organic acids that are not unduly toxic. For example, acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenyl acetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—(CH2)n-COOH where n is 0-4, and the like, or using a different acid that produces the same counterion. Lists of additional suitable salts may be found, for example, in Remington's Pharmaceutical Sciences, 17th ed., Mack Publishing Company, Easton, Pa., p. 1418 (1985).

The term $C_2$-$C_8$ ether refers to a straight/branched and/or cyclic/acyclic ether having any of the number of carbons within the range, and the range is specifically intended to independently disclose each compound within the range. The $C_2$-$C_8$ ether includes, but is not limited to, dimethyl ether, diethyl ether, di-isopropyl ether, di-n-butyl ether, methyl-t-butyl ether (MTBE), tetrahydrofuran, and dioxane.

The term $C_3$-$C_7$ ketone refers to a straight/branched and/or cyclic/acyclic ketone having any of the number of carbons within the range, and the range is specifically intended to independently disclose each compound within the range. The $C_3$-$C_7$ ketone includes, but is not limited to, acetone, methyl ethyl ketone, propanone, butanone, methyl isobutyl ketone, methyl butyl ketone, and cyclohexanone.

The term $C_2$-$C_7$ nitrile refers to a nitrile having any of the number of carbons within the range, and the range is specifically intended to independently disclose each compound within the range. The $C_2$-$C_7$ nitrile includes, but is not limited to, acetonitrile and propionitrile.

The term $C_1$-$C_8$ alcohol refers to a straight/branched or cyclic/acyclic alcohol having any of the number of carbons within the range, and the range is specifically intended to independently disclose each compound within the range. The $C_1$-$C_8$ ketone includes, but is not limited to, methanol, ethanol, n-propanol, isopropanol, isobutanol, hexanol, and cyclohexanol.

The term $C_1$-$C_2$ chlorocarbon refers to a chlorocarbon with 1-2 carbons, with any number of chloro atoms that fulfill the desired purpose. The $C_1$-$C_2$ chlorocarbon includes, but is not limited to, chloroform, dichloromethane (DCM), carbon tetrachloride, 1,2-dichloroethane, and tetrachloroethane, Also described herein, in an alternative embodiment, is a process for synthesizing (E)-1,2-di(thiophen-2-yl)ethene-1,2-diol compounds of Formula I wherein the process comprises the coupling of two carbaldehyde compounds of Formula Ia in the presence of a Cu(II) catalyst:

wherein $R^1$, $R^2$, and $R^3$ are independently selected from: hydrogen, alkyl, alkoxy, —CN, halogen, and —NO$_2$.

In another aspect, the method is the synthesis of (E)-1,2-di(thiophen-2-yl)ethene-1,2-diol compounds of Formula I comprising the steps of (1) the coupling of two molecules of Formula Ia in the presence of a Cu(II) catalyst to afford crude compound of Formula I:

and
(2) further optionally purifying the crude compound of Formula I from step (1) to afford pure compound of Formula I.

In one embodiment, $R^1$ is alkyl, including, but not limited to methyl, ethyl, or propyl. In one embodiment, $R^1$ is alkoxy, including, but not limited to methoxy, ethoxy, or propoxy. In one embodiment, $R^1$ is —CN. In one embodiment, $R^1$ is —NO$_2$. In one embodiment, $R^1$ is —NO$_2$. In one embodiment, $R^2$ is halogen, for example, F, Cl, or Br.

In one embodiment, $R^2$ is alkyl, including, but not limited to methyl, ethyl, or propyl. In one embodiment, $R^2$ is alkoxy, including, but not limited to methoxy, ethoxy, or propoxy. In one embodiment, $R^2$ is —CN. In one embodiment, $R^2$ is —NO$_2$. In one embodiment, $R^2$ is halogen, for example, F, Cl, or Br.

In one embodiment, $R^3$ is alkyl, including, but not limited to methyl, ethyl, or propyl. In one embodiment, $R^3$ is alkoxy, including, but not limited to methoxy, ethoxy, or propoxy. In one embodiment, $R^3$ is —CN. In one embodiment, $R^3$ is —NO$_2$. In one embodiment, $R^2$ is —NO$_2$. In one embodiment, $R^3$ is halogen, for example, F, Cl, or Br.

Non-limiting examples of a compound of Formula Ia include:

Additional non-limiting examples of a compound of Formula Ia include:

-continued

Non-limiting examples of a compound of Formula I prepared by the methods described herein include:

-continued

Additional non-limiting examples of a compound of Formula I prepared by the methods described herein include:

Additional non-limiting examples of a compound of Formula I prepared by the methods described herein include:

-continued

Also described herein is a process for synthesizing (E)-1,2-di(pyridin-2-yl)ethene-1,2-diol wherein the process comprises the coupling of two molecules of picolinaldehyde in the presence of a homogenous Cu(II) complex of 1,10-phenanthroline (phen) and diamine (a copper(II)/phen/diamine catalyst) of Formula A:

wherein:

n is an integer selected from 1 and 2;

R is independently selected from —H, —CH$_3$, and —CH$_2$CH$_2$OH; and

X$^-$ is Cl$^-$, Br$^-$, or NO$_3^-$.

In another aspect, the method is the synthesis of (E)-1,2-di(pyridin-2-yl)ethene-1,2-diol comprising the steps of (1) the coupling of two molecules of picolinaldehyde in the presence of a homogenous Cu(II) complex of 1,10-phenanthroline (phen) and diamine (a copper(II)/phen/diamine catalyst) of Formula A to afford crude (E)-1,2-di(pyridin-2-yl)ethene-1,2-diol:

-continued (2) further optionally purifying crude (E)-1,2-di(pyridin-2-yl)ethene-1,2-diol from step (1) to afford pure (E)-1,2-di(pyridin-2-yl)ethene-1,2-diol;

wherein:

n is an integer selected from 1 and 2;

R is independently selected from —H, —CH$_3$, and —CH$_2$CH$_2$OH; and

X$^-$ is Cl$^-$, Br$^-$, or NO$_3^-$.

In certain embodiments, the pure (E)-1,2-di(pyridin-2-yl)ethene-1,2-diol product is about 93% or greater the E-isomer over the Z-isomer, about 95% or greater the E-isomer over the Z-isomer, about 97% or greater the E-isomer over the Z-isomer, about 98% or greater the E-isomer over the Z-isomer, about 99% or greater the E-isomer over the Z-isomer, or even about 100% the E-isomer over the Z-isomer.

In one embodiment, the synthesis of (E)-1,2-di(pyridin-2-yl)ethene-1,2-diol is conducted at room temperature.

In one embodiment, the synthesis of (E)-1,2-di(pyridin-2-yl)ethene-1,2-diol is conducted in an aqueous medium. In certain embodiments, the synthesis is conducted in a polar aprotic solvent/water system, including, but not limited to tetrahydrofuran (THF)/water, acetone/water, DMF/water, ACN/water, and DMSO/water. In one embodiment, the synthesis is conducted in THF/water. In certain embodiments, the ratio of polar aprotic solvent:water is about 4:1, about 3:1, about 2:1, about 1:1, about 1:2, about 1:3, or about 1:4. In one embodiment, the ratio of polar aprotic solvent:water is about 1:1.

In one embodiment, the amount of the Cu(II) catalyst of Formula A is between about 0.05% and 10.0%, between about 0.1% and 5.0%, between about 0.5% and 3.0%, between about 1.0% and 5.0%, or between about 3.0% and 5.0% by weight of picolinaldehyde. In one embodiment, the amount of the Cu(II) catalyst of Formula A is between about 0.25% and 3.0%, between about 0.25% and 2.0%, or between about 0.25% and 1.5% by weight of picolinaldehyde. In one embodiment, the amount of the Cu(II) catalyst Formula A is between about 3.0% and 10.0%, between about 4.0% and 9.0%, or between about 5.0% and 8.0% by weight of picolinaldehyde. In one embodiment, the amount of the Cu(II) catalyst Formula A is between about 3.0% and 5.0% by weight of picolinaldehyde. In one embodiment, the amount of the Cu(II) catalyst Formula A is about 1.0% by weight of picolinaldehyde.

Also described herein, in an alternative embodiment, is a process for synthesizing (E)-1,2-di(pyridin-2-yl)ethene-1,2-diol compounds of Formula II comprising the coupling of two carbaldehyde compounds of Formula IIa in the presence of a homogenous Cu(II) complex of 1,10-phenanthroline (phen) and diamine (a copper(II)/phen/diamine catalyst) of Formula A:

wherein
1 or 2 of $X^1$-$X^5$ are N and the remaining are CH;
n is an integer selected from 1 and 2;
R is independently selected from —H, —CH$_3$, and —CH$_2$CH$_2$OH; and
$X^-$ is Cl$^-$, Br$^-$, or NO$_3^-$.

In another aspect, the method is the synthesis of (E)-1,2-di(pyridin-2-yl)ethene-1,2-diol compounds of Formula II comprising the steps of (1) the coupling of two molecules of Formula IIa in the presence of a homogenous Cu(II) complex of 1,10-phenanthroline (phen) and diamine (a copper (II)/phen/diamine catalyst) of Formula A to afford an crude (E)-1,2-di(pyridin-2-yl)ethene-1,2-diol compound of Formula II:

and
(2) further optionally purifying the compound of Formula II from step (1) to afford pure (E)-1,2-di(pyridin-2-yl)ethene-1,2-diol compound of Formula II;

wherein
1 or 2 of $X^1$-$X^5$ are N and the remaining are CH;
n is an integer selected from 1 and 2;
R is independently selected from —H, —CH$_3$, and —CH$_2$CH$_2$OH; and
$X^-$ is Cl$^-$, Br$^-$, or NO$_3^-$.

Non-limiting examples of a compound of Formula II include:

EXAMPLES

The melting point was determined on Gallenkamp electronic melting point apparatus. The infrared spectra were recorded on a Mattson 5000 Fourier transform-IR (FT-IR) spectrophotometer. The $^1$H-NMR spectra were determined on a JOEL™ 600 MHz NMR spectrometer, Japan using TMS as internal standard and chloroform (CDCl$_3$). The mass spectra were recorded on a 70 eV Kratos MS. Elemental analysis was carried out using Elementar Analysensysteme GmbH Vario EL III.

Example 1. Synthesis of the Cu(II) Complex of Formula A

To synthesize the Cu(II) complex of Formula A, 1 mmol of $CuX_2 \cdot 6H_2O$ (X=Cl, Br or $NO_3$) was dissolved in 50 mL of ethanol and the reaction mixture was treated with 1 mmol of phenanthroline (phen) followed by 1 mmol of the diamine. The reaction was subjected to room temperature stirring for 2 hours until the blue desired complex was precipitated. The solid complex was filtrated and washed several times with 50 mL of n-hexane and dichloromethane.

Figure 2:
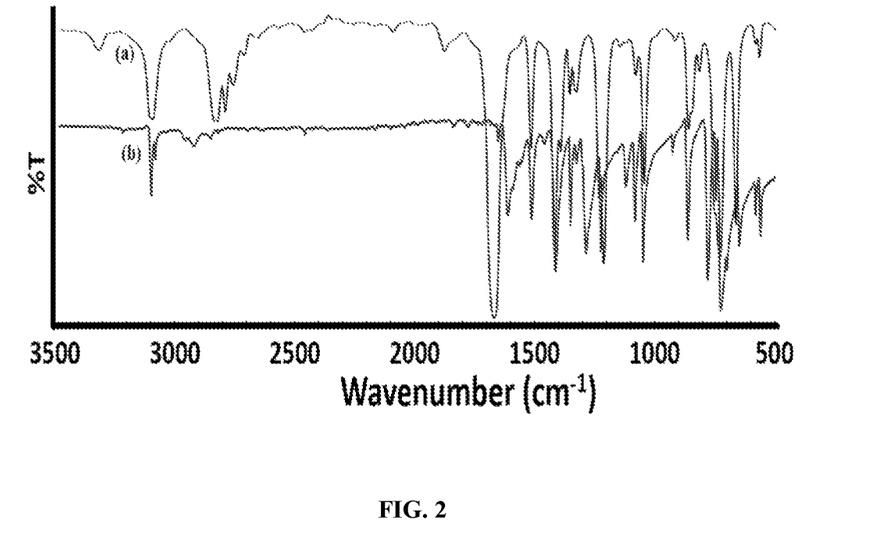
FIG. 2 illustrates solid state FT-IR spectra recorded for (a) the starting material: thiophene-2-carbaldehyde and (b) the product: (E)-1,2-di(thiophen-2-yl)ethene-1,2-diol measured as described herein in the Examples. The FT-IR-spectra of the diol product together with thiophene-2-carbaldehyde starting material indicates that the vibration frequencies of each functional group appeared at their expected positions. The disappearance of the aldehyde's C=O and C—H parallel to the appearing of O—H bending band confirmed the coupling of two aldehydes together to form (E)-1,2-di(thiophen-2-yl)ethene-1,2-diol. The absence of vibration of O—H vinyl group is due to the strong intramolecular-hydrogen bond formation (Al-Zaqri, N., et al., *Journal of Coordination Chemistry*, 2020: p. 1-13).
Figure 3:
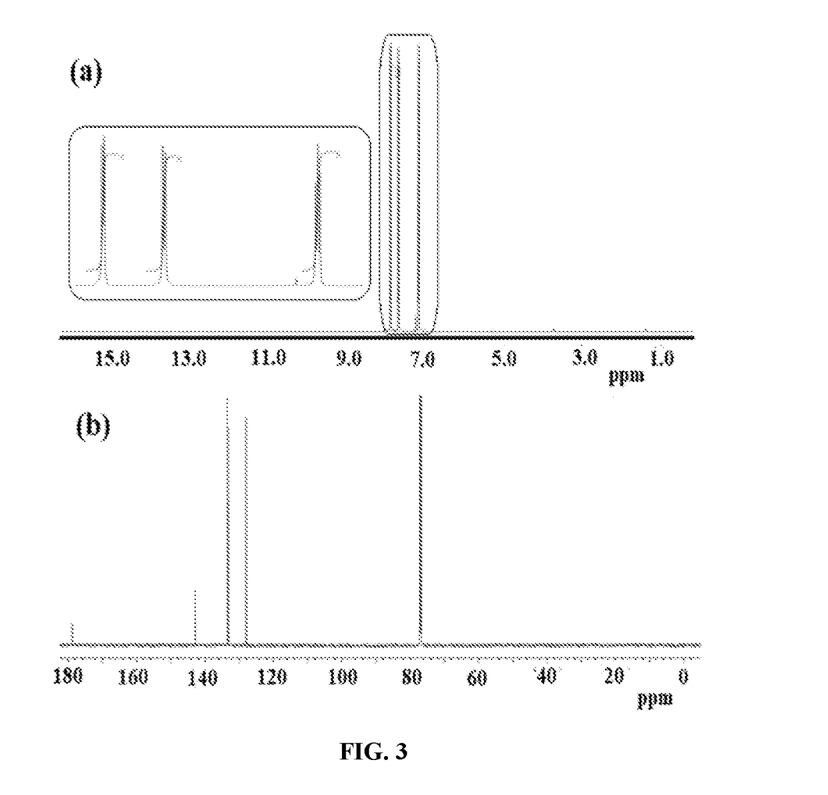
FIG. 3 shows (a) $^1$H NMR and (b) $^{13}$C NMR spectra of (E)-1,2,-di(thiophen-2-yl)ethene-1,2-diol recorded in CDCl$_3$ at room temperature measured as described herein in the Examples. The $^1$H-NMR spectrum of the diol product identifies three signals of CH aromatic protons detected at 7.1 ppm (dd), 7.7 ppm (d) and 7.9 ppm (d). The absence of OH protons may be due to D/H exchange. Four signals related to the aromatic C—H were also observed at 128-133 ppm. The chemical shifts of the aromatic C at 146 ppm and =COH at 176 ppm.
Figure 4:
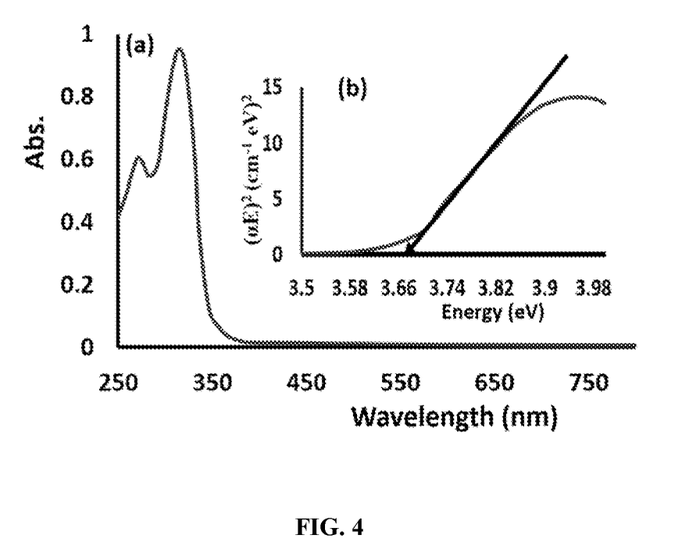
FIG. 4 provides (a) UV-Vis spectra and (b) Optical band gap (Tauc's plot) of (E)-1,2,-di(thiophen-2-yl)ethene-1,2-diol dissolved in DMSO at room temperature measured as described herein in the Examples. The UV-Vis spectra of the diol product indicates that completeness of the reaction as supported by (π→π*)/(n→π*) UV absorption changes at $\lambda_{max}$=275 and 320 nm, respectively. No peak above 350 nm was detected. The Tauc's equation is applied to determine the optical activity behavior of the produced diol in methanol. The ΔEg of the compound was determined to be 3.68 ev.
Figure 5:
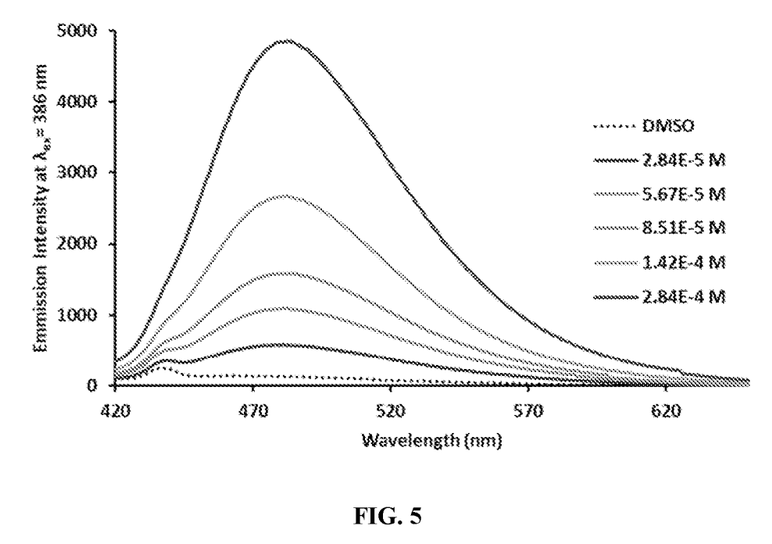
FIG. 5 shows emission spectra (at 386 nm excitation) of (E)-1,2-di(thiophen-2-yl)ethene-1,2-diol in DMSO at varying concentrations measured as described herein in the Examples. The emission spectra of the produced diol exhibited a maxima at 483 nm. Possessing a good ability to fluoresce, the produced diol is expected to find important applications as sensors for heavy metals in groundwater and other aqueous media.
Figure 6:
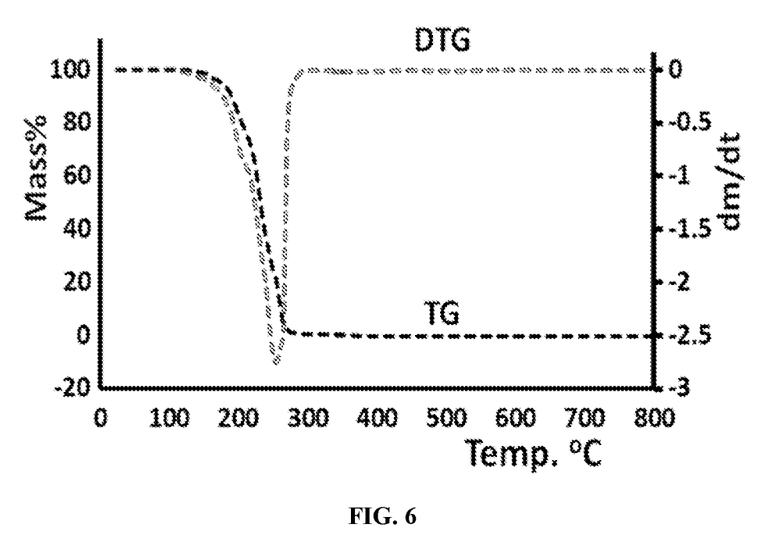
FIG. 6 shows Thermogravimetry/Differential Thermal Analysis (TG/DTG) of (E)-1,2-di(thiophen-2-yl)ethene-1,2-diol diol measured as described herein in the Examples. The TG/DTG analyses was performed at a heat rate of 10 min/° C. and the sample was found to be stable up to 150° C. and decomposed in one step process.

Example 2. Synthesis of (E)-1,2-di(thiophen-2-yl)ethene-1,2-diol (E)-1,2-di(thiophen-2-yl)ethene-1,2-diol was synthesized by mixing thiophene-2-carbaldehyde (0.5 g, 4.5 mmol) in 20 mL $THF/H_2O$ (1:1) with a homogenous Cu(II) complex of 1,10-phenanthroline (phen) and diamine (a copper(II)/phen/diamine catalyst) of Formula A (0.005 g, 0.12 mmol) dissolved in 2 mL THF. The mixture was stirred at room temperature for 12 hours. The solvent was allowed to evaporate at room temperature and the resulting product was mixed with 100 mL $H_2O/DCM$ (1:1) inside a separatory funnel. The mixture was shaken for 15 minutes and allowed to separate into two layers over the course of 1 hour. The organic layer that contained the product was separated and the solvent was allowed to evaporate. The produced material was collected as a colorless powder with a melting point of 140° C. and a yield of 88%. FT-IR ($\upsilon/cm^{-1}$): 3100-3010 (C—$H_{thiophen}$), 2980-2820 (H—C=C), 1661 (H—$O_{bending}$), see FIG. 2; $^1H$ NMR (600 MHz, $CDCl_3$): δ/ppm: 7.1 (dd, 2H), 7.7 (d, 2H), 7.9 (d, 2H). $^{13}C$-NMR (151 MHz, $CDCl_3$), 128 (2×$CH_{thienyl}$), 132 (2×$CH_{thienyl}$), 133 (2×$CH_{thienyl}$), 146 (2×$C_{thienyl}$), 176 (2×=C(OH)), see FIG. 3. Anal. Calcd. for $C_{10}H_8O_2S_2$: C, 53.55; H, 3.59%. Found: C, 53.44; H, 3.47%. The MS m/z 224 [$M^+$] (224.29 theoretical), see FIG. 1.

According to the $^1H$-NMR, no Z-isomer was detected and, therefore 100% of the detected isomer was the E-isomer

The composition of (E)-1,2-di(thiophen-2-yl)ethene-1,2-diol was confirmed by elemental analysis as well as TOF-MS. The elemental analysis reflected the presence of 53.44% C and 3.47% H compared to calculated 53.55% and 3.59% H for $C_{10}H_8O_2S_2$.

Figure 1:
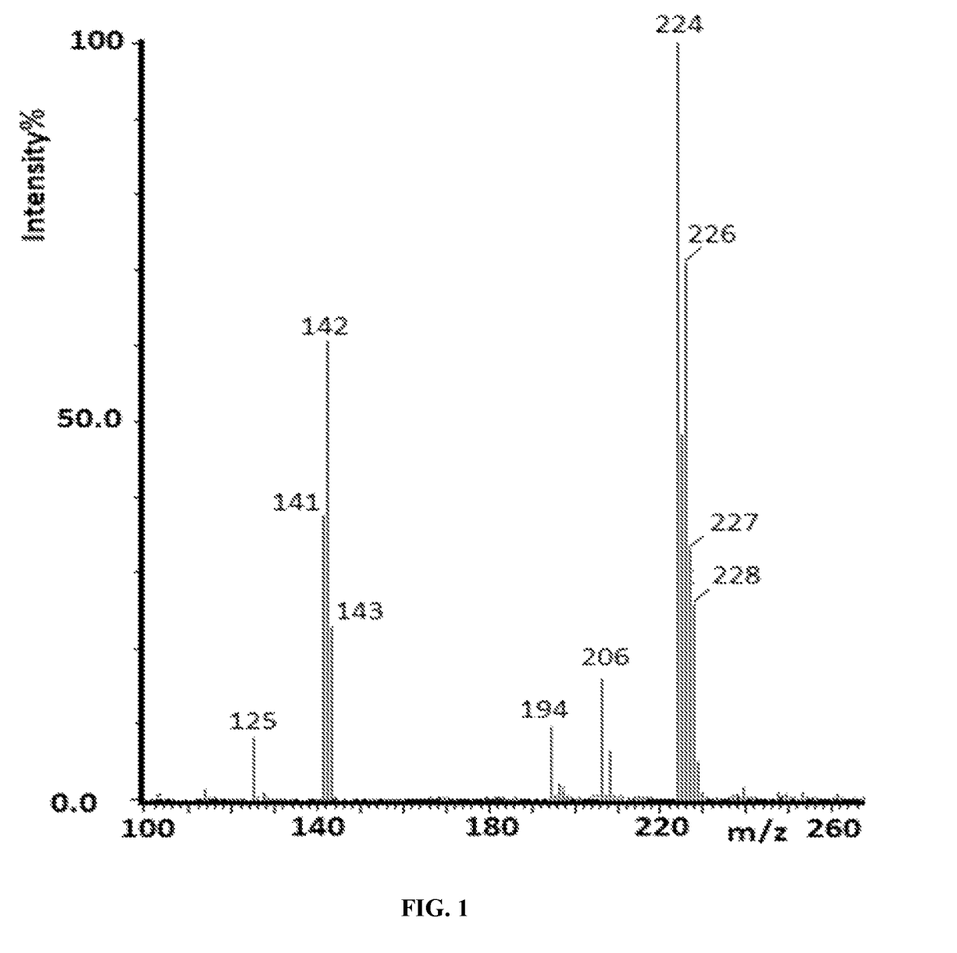
FIG. 1 illustrates the TOF-MS of (E)-1,2,-di(thiophen-2-yl)ethene-1,2-diol measured as described herein in the Examples.

The MS showed the $M^+$=224 mz (theoretical 224.29 m/z). FIG. 1 illustrates the TOF-MS of (E)-1,2-di(thiophen-2-yl) ethene-1,2-diol. The MS spectrum confirmed the formation of the desired compound.

The previous detailed description is of a small number of embodiments for implementing the invention and is not intended to be limiting in scope. One of skill in this art will immediately envisage the methods and variations used to implement this invention in other areas than those described in detail. The following claims set forth a number of the embodiments of the invention disclosed with greater particularity.

What is claimed is:

1. A process for synthesizing (E)-1,2-di(thiophen-2-yl) ethene-1,2-diol from the dimerization of thiophene-2-carbaldehyde in the presence of a Cu(II) catalyst:

2. The process of claim 1, wherein the Cu(II) catalyst is a Cu(II) complex of Formula A:

wherein:
n is an integer selected from 1 and 2;
R is independently selected from —H, —$CH_3$, and —$CH_2CH_2OH$; and
$X^-$ is $Cl^-$, $Br^-$, or $NO_3^-$.

3. The process of claim 2, wherein the complex of Formula A is of the structure:

or

4. The process of claim 3, wherein the complex of Formula A is of the structure:

or

5. The process of claim 3, wherein the complex of Formula A is of the structure:

or

6. The process of claim 3, wherein the complex of Formula A is of the structure:

7. The process of claim 1, wherein the dimerization is conducted in an aqueous medium.

8. The process of claim 1, wherein the dimerization is conducted in a polar aprotic solvent/water system.

9. The process of claim 1, wherein the dimerization is conducted in a polar aprotic solvent.

10. The process of claim 8, wherein the polar aprotic solvent is THF.

11. The process of claim 8, wherein the polar aprotic solvent is acetone.

12. The process of claim 8, wherein the polar aprotic solvent is acetonitrile.

13. The process of claim 8, wherein the polar aprotic solvent is DMSO or DMF.

14. The process of claim 1, wherein the amount of the Cu(II) catalyst is between about 0.1% and 10% by weight of the thiophene-2-carbaldehyde.

15. The process of claim 14, wherein the amount of the Cu(II) catalyst is between about 0.1% and 5% by weight of the thiophene-2-carbaldehyde.

16. The process of claim 14, wherein the amount of the Cu(II) catalyst is between about 0.5% and 3% by weight of the thiophene-2-carbaldehyde.

17. The process of claim 14, wherein the amount of the Cu(II) catalyst is at least about 0.5% by weight of the thiophene-2-carbaldehyde.

18. The process of claim 14, wherein the amount of the Cu(II) catalyst is at least about 1% by weight of the thiophene-2-carbaldehyde.

19. The process of claim 14, wherein the amount of the Cu(II) catalyst is about 1% by weight of the thiophene-2-carbaldehyde.

20. The process of claim 1, wherein the dimerization is conducted at room temperature.

21. The process claim 1, wherein the process affords a substantially pure form of (E)-1,2-di(thiophen-2-yl)ethene-1,2-diol that is greater than about 95% the E-isomer.

22. The process of claim 1, wherein the process affords a substantially pure form of (E)-1,2-di(thiophen-2-yl)ethene-1,2-diol that is about 100% the E-isomer.

* * * * *